US010179957B1

(12) United States Patent
Dunaway et al.

(10) Patent No.: US 10,179,957 B1
(45) Date of Patent: Jan. 15, 2019

(54) METHODS AND SYSTEMS FOR X-RAY INSPECTION OF PDC TOOLING AND PARTS

(71) Applicant: US SYNTHETIC CORPORATION, Orem, UT (US)

(72) Inventors: Tyler Scott Dunaway, Pleasant Grove, UT (US); Greg Carlos Topham, Spanish Fork, UT (US); Renato Ventura, Provo, UT (US)

(73) Assignee: US SYNTHETIC CORPORATION, Orem, UT (US)

( * ) Notice: Subject to any disclaimer, the term of this patent is extended or adjusted under 35 U.S.C. 154(b) by 294 days.

(21) Appl. No.: 15/068,472

(22) Filed: Mar. 11, 2016

Related U.S. Application Data

(60) Provisional application No. 62/132,965, filed on Mar. 13, 2015.

(51) Int. Cl.
*G06K 9/00* (2006.01)
*C25F 7/00* (2006.01)
*G01N 23/04* (2018.01)
*C25F 3/02* (2006.01)

(52) U.S. Cl.
CPC .............. *C25F 7/00* (2013.01); *C25F 3/02* (2013.01); *G01N 23/04* (2013.01)

(58) Field of Classification Search
CPC ...... E21B 10/46; G01N 23/18; G01N 23/083; G01N 23/04; G01R 31/302; B32B 3/26; B24B 3/00; B24B 3/06; B24B 3/08; B24B 3/10; G21K 1/02; G06F 19/00; C25F 7/00; C25F 3/02
See application file for complete search history.

(56) References Cited

U.S. PATENT DOCUMENTS

| | | | | | |
|---|---|---|---|---|---|
| 4,241,135 | A | * | 12/1980 | Lee | B01J 3/062 419/11 |
| 4,925,701 | A | * | 5/1990 | Jansen | C23C 16/0272 427/162 |
| 9,037,430 | B1 | * | 5/2015 | Wiggins | G01N 27/041 702/45 |
| 2002/0011852 | A1 | * | 1/2002 | Mandelis | G01R 31/311 324/750.02 |
| 2010/0089663 | A1 | * | 4/2010 | Corbett | E21B 10/567 175/428 |

(Continued)

OTHER PUBLICATIONS

U.S. Appl. No. 13/267,026, filed Oct. 6, 2011, Mukhopadhyay et al.

(Continued)

*Primary Examiner* — Amir Alavi

(74) *Attorney, Agent, or Firm* — Dorsey & Whitney LLP

(57) ABSTRACT

Embodiments disclosed herein are directed to methods and systems for X-ray imaging and/or inspection of a PCD element in a protective leaching cup, which may be placed in a tray. Embodiments include inspection of one or more characteristics between the protective leaching cup and the PCD element prior to and/or after leaching of the PCD element. Embodiments also include using X-ray imaging to assist with positioning the PCD element in the protective leaching cup. Embodiments further include inspection of one or more defects in the PCD element during processing and/or after usage by X-ray technique.

17 Claims, 12 Drawing Sheets

(56) References Cited

U.S. PATENT DOCUMENTS

| | | | | |
|---|---|---|---|---|
| 2012/0037430 A1* | 2/2012 | Smallman | ............... | C22C 26/00 |
| | | | | 175/428 |
| 2015/0110244 A1* | 4/2015 | Tsujino | ................. | G01N 23/06 |
| | | | | 378/58 |
| 2015/0162161 A1* | 6/2015 | Yamada | ................. | H01J 35/08 |
| | | | | 378/62 |
| 2015/0303022 A1* | 10/2015 | Yamada | ................. | H01J 35/08 |
| | | | | 378/62 |
| 2017/0268296 A1* | 9/2017 | Gledhill | ................ | B24D 18/00 |

OTHER PUBLICATIONS

U.S. Appl. No. 14/084,058, filed Nov. 19, 2013, Gleason et al.
U.S. Appl. No. 14/086,283, filed Nov. 21, 2013, Knuteson et al.
U.S. Appl. No. 14/304,631, filed Jun. 13, 2014, Mukhopadhyay et al.
U.S. Appl. No. 62/096,315, filed Dec. 23, 2014, Heaton et al.
U.S. Appl. No. 62/132,965, filed Mar. 13, 2015, Dunaway et al.

* cited by examiner

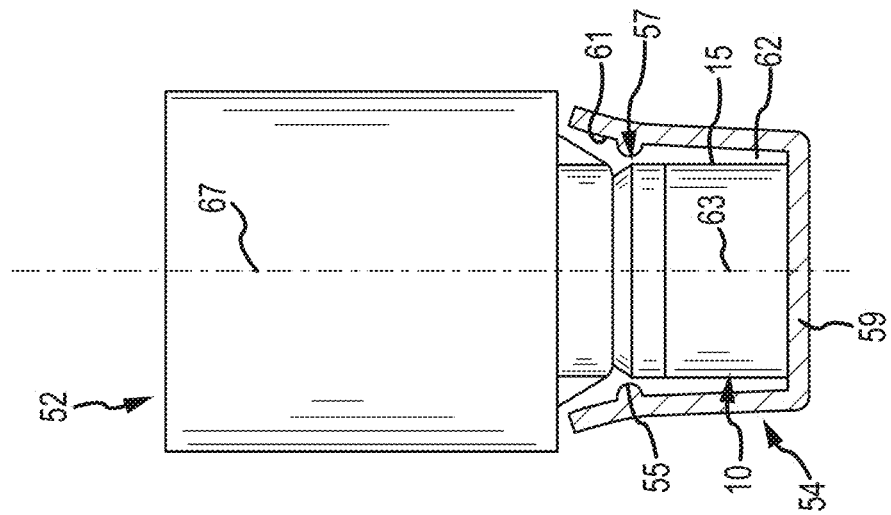
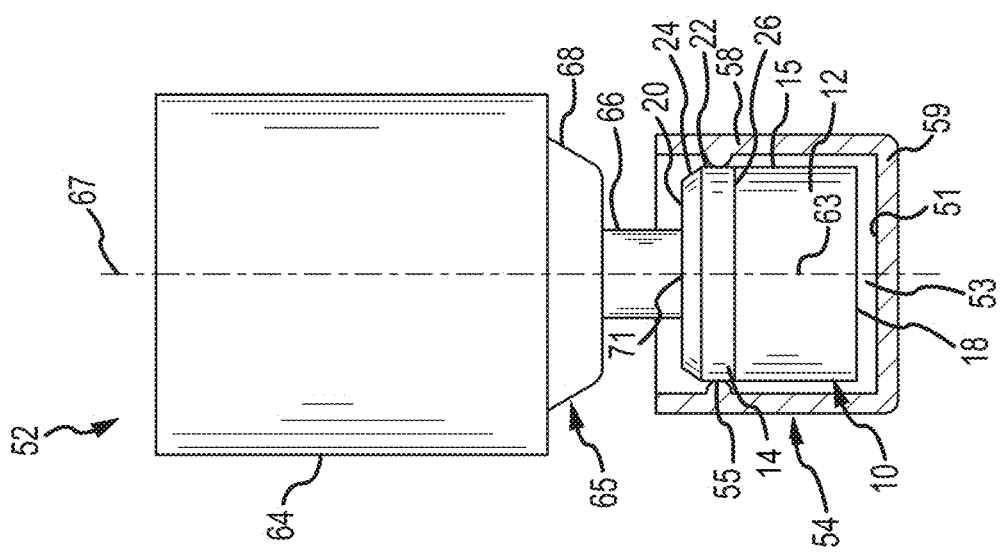

METHODS AND SYSTEMS FOR X-RAY INSPECTION OF PDC TOOLING AND PARTS

CROSS-REFERENCE TO RELATED APPLICATIONS

This application claims priority to U.S. Provisional Application No. 62/132,965 filed on 13 Mar. 2015, the disclosure of which is incorporated herein, in its entirety, by this reference.

BACKGROUND

Wear-resistant, superabrasive materials are traditionally utilized for a variety of mechanical applications. For example, polycrystalline diamond ("PCD") materials are often used in drilling tools (e.g., cutting elements, gage trimmers, etc.), machining equipment, bearing apparatuses, wire-drawing machinery, and in other mechanical systems.

Cutting elements that have a superabrasive layer or a PCD table may be formed and bonded to a substrate using an ultra-high pressure, ultra-high temperature ("HPHT") sintering process to form a polycrystalline diamond compact ("PDC"). Often, cutting elements that have a PCD table are fabricated by placing a cemented carbide substrate, such as a cobalt-cemented tungsten carbide substrate, into a container or cartridge with a volume of diamond particles positioned on a surface of the cemented carbide substrate. The substrate and diamond particle volumes may then be processed under diamond-stable HPHT conditions in the presence of a catalyst material, which causes the diamond particles to bond to one another to form a diamond table having a matrix of bonded diamond grains. The catalyst material is often a metal-solvent catalyst, such as cobalt, nickel, or iron, which facilitates intergrowth and bonding of the diamond crystals. The catalyst may come from the cemented-carbide substrate, such as cobalt from a cobalt-cemented tungsten carbide substrate, which liquefies and sweeps from a region adjacent to the volume of diamond particles into interstitial regions between the diamond particles during the HPHT process.

The presence of the metal-solvent catalyst and/or other materials in the diamond table may reduce a thermal stability of the diamond table at elevated temperatures. For example, a difference in the thermal expansion coefficient between the diamond grains and the metal-solvent catalyst is believed to lead to chipping or cracking in the PCD table of a cutting element during drilling or cutting operations. The chipping or cracking in the PCD table may degrade the mechanical properties of the cutting element or lead to failure of the cutting element. Additionally, at high temperatures, diamond grains may undergo a chemical breakdown or back-conversion with the metal-solvent catalyst. Further, portions of diamond grains may transform to carbon monoxide, carbon dioxide, graphite, or combinations thereof, thereby degrading the mechanical properties of the PCD material. Accordingly, it is desirable to remove a metal-solvent catalyst from a PCD material in situations when the PCD table or material may be exposed to high temperatures.

Chemical leaching is often used to dissolve and remove the metal-solvent catalyst from the PCD table. Conventional chemical leaching techniques often involve the use of highly concentrated and corrosive leaching solutions, such as highly acidic solutions, to dissolve and remove metal-solvent catalysts from polycrystalline diamond materials.

However, the leaching solutions may dissolve any accessible portions of the substrate to which the PCD table is attached. For example, highly acidic leaching solutions may dissolve any accessible portions of the cobalt-cemented tungsten carbide substrate, causing undesired pitting and/or other corrosion of the substrate surface.

U.S. patent application Ser. No. 14/084,058, entitled "Protective Leaching Cups, Systems, and Methods of Use," filed on 19 Nov. 2013, discloses that a polymeric leaching cup may be placed around a portion of a PCD element or layer to protect the substrate from the leaching solutions. The polymeric leaching cup may, for example, surround the substrate surface and a portion of the PCD layer near the substrate. The entire disclosure of the U.S. patent application Ser. No. 14/084,058 is incorporated herein by reference.

U.S. patent application Ser. No. 14/084,058 also discloses an expansion apparatus for positioning a superabrasive element within a protective leaching cup and/or for expanding a portion of the protective leaching cup to at least partially evacuate gas(es) trapped between the superabrasive element and the protective leaching cup by expanding or bending a top portion of the protective leaching cup. The gas(es), such as air, may be trapped between the protective leaching cup and a PDC when the cup is placed around the PDC. During leaching, trapped gas(es) may expand due to an increase in temperature and/or a decrease in pressure, pushing the PDC out of the leaching cup and exposing a portion of the substrate or other protected part of the PDC to the leaching solution. Such exposure to leaching solutions may result in undesired corrosion and/or damage to the substrate.

Therefore, manufactures and users of PDCs continue to seek improved PDC processing techniques.

SUMMARY

Embodiments disclosed herein are directed to methods and systems for imaging and/or inspection of a PCD element in a protective leaching cup, which may be placed in a tray. Embodiments include inspection of one or more sealing characteristics between the protective leaching cup and the PCD element prior to leaching of the PCD element. Embodiments also include using imaging to assist with positioning the PCD element in the protective leaching cup. Embodiments further include inspection of one or more defects in the PCD element during processing and/or after usage by an imaging technique such as X-ray imaging.

In an embodiment, a method of inspecting a PCD element prior to leaching is disclosed. The PCD element in a protective leaching cup is provided, with the protective leaching cup configured to expose a selected portion of the PCD element to a leaching agent. An X-ray image of the PCD element in the protective leaching cup is captured. The X-ray image is analyzed to determine one or more characteristics of the protective leaching cup against the PCD element.

In an embodiment, a method of leaching a PCD element and inspecting the leached PCD element is disclosed. The PCD element in a protective leaching cup is at least partially leached according to a first method. An X-ray image of the leached PCD element in the protective leaching cup is captured. The X-ray image is analyzed to determine at least one characteristic of a first leached region of the leached PCD element. The leached PCD element in the protective leaching cup is at least partially leached according to a second method, or the leached PCD element is removed from the protective leaching cup after the act of analyzing the X-ray image.

In an embodiment, another method of leaching a PCD element and inspecting a leached PCD element is disclosed. A first X-ray image of a PCD element in a protective leaching cup is captured. The PCD element is at least partially leached to form a leach profile therein. A second X-ray image of the PCD element in the leaching cup is captured. If the leach profile of the PCD is satisfactory at least partially based on the second X-ray image, the PCD element is removed from the protective leaching cup. If the leach profile of the PCD element is not satisfactory at least partially based on the second X-ray image, the PCD element may be re-leached or the protective leaching cup may be rejected.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

For better understanding, like elements have been designated by like reference numbers throughout the various accompanying figures. Understanding that these drawings depict only typical embodiments of the disclosure and are not therefore to be considered to be limiting of its scope, the embodiments of the disclosure will be described and explained with additional specificity and detail through the use of the accompanying drawings in which:

FIG. 4A is a side view of an assembly that includes a PDC and an expansion apparatus positioned within a protective leaching cup in a first position for X-ray inspection according to an embodiment;

FIG. 4B is a side view of another assembly that includes the PDC and the expansion apparatus of FIG. 4A positioned in a second position for X-ray inspection according to an embodiment;

DETAILED DESCRIPTION

Figure 1:
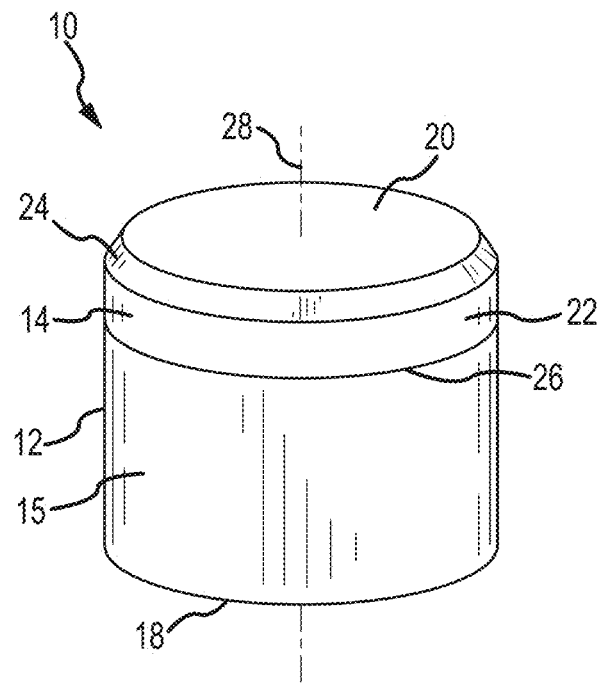
FIG. 1 is an isometric view of a PDC according to an embodiment.

Embodiments of the disclosure relate to PCD elements (e.g., freestanding PCD tables, PDCs, etc.) that may include a PCD table or other PCD feature, and methods of fabricating the PCD element including leaching the PCD element using a protective leaching cup. The disclosed PDCs and PCD elements may be used in a variety of applications, such as rotary drill bits, machining equipment, and other articles and apparatuses. The PCD elements, as disclosed herein, may also be used as bearing elements in a variety of bearing applications, such as thrust bearings, radial bearing, and other bearing apparatuses, without limitation.

More specifically, embodiments disclosed herein are directed to methods and systems for X-ray imaging and/or inspection of a PCD element in a protective leaching cup, which may be placed in a tray that may hold multiple protective leaching cups. In some embodiments, the X-ray imaging and/or inspection may assist with understanding or evaluating a sealed region formed between the PCD element and the protective leaching cup holding the PCD element prior to leaching. For example, the X-ray inspection may be used to measure and/or determine where the protective leaching cup seals against the PCD element to control a leach depth profile of the PCD element prior to leaching.

In some embodiments, the X-ray inspection may also assist with, prior to leaching, inspecting to determine if there are trapped gas(es) between the PCD element and the protective leaching cup. For example, the X-ray inspection may determine a presence of and/or measure a gap between a bottom of the PCD element and a base portion of the protective leaching cup in which the PCD element is held. If the trapped gas(es) are present as may be manifested by the gap, the X-ray imaging may also assist with aligning an expansion apparatus with the protective leaching cup before forcing the expansion apparatus against the PCD element to enable removal of the trapped gas(es) and the gap. In some embodiments, X-ray inspection may occur after leaching, but while the leaching cup is still assembled with the PCD element. Re-leaching the PCD element while the leaching cup is assembled with the PCD element, may be performed after the X-ray inspection. The X-ray inspection may be used for quality control, for example, to detect leaks in the protective leaching cup or to measure leach depth and/or profile in the leached PCD element.

In some embodiments, the X-ray inspection may further assist with analyzing and comparing different protective leaching cups and/or fixtures formed from various materials and/or geometries to select one type of protective leaching cup that provides a specified leaching profile for the PCD element and may protect a substrate to which the PCD element is bonded better than other protective leaching cups. For example, the X-ray inspection may be used for viewing clusters or agglomerations in the PCD element, cracks, pits, or abnormal grain growth ("AGG") of tungsten carbide ("WC") in the substrate (e.g. WC plumes). The selected protective leaching cup may yield fewer defects during leaching of the PCD element.

Figure 2:
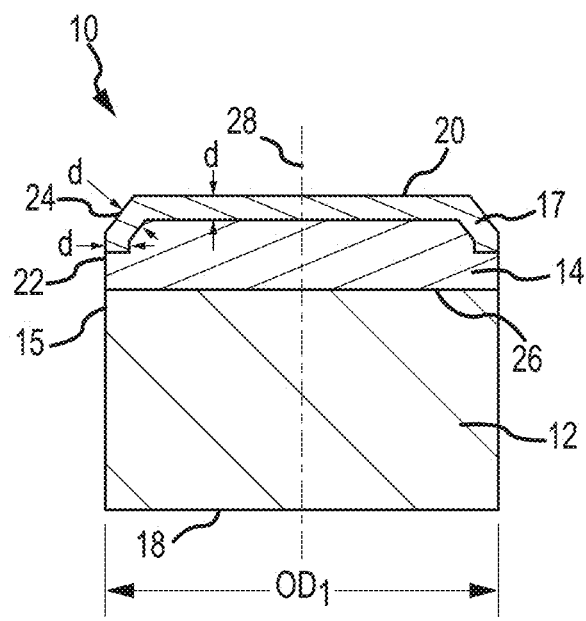
FIG. 2 is cross-sectional view of the PDC illustrated in FIG. 1.

FIGS. 1 and 2 illustrate a PDC 10 according to an embodiment. The PDC 10 is an example of a superabrasive element that may be leached when held in a protective leaching cup and inspected using an X-ray system and imaging method according to one or more of the disclosed embodiments as discussed in more detail below. The PDC 10 may include a PCD table 14 bonded to and/or formed upon a substrate 12 with an interface 26 therebetween. The PDC 10 may include a rear face 18, a superabrasive face 20, at least one side surface 15 of the substrate 12, and at least one PCD side surface 22 formed by the PCD table 14. The PCD table 14 may also include a chamfer 24, which includes an angular and/or rounded edge formed at an intersection of the PCD side surface 22 and the superabrasive face 20. The chamfer 24 may help define a leached depth of the PCD table 14.

The PDC 10 may exhibit any suitable size, shape, geometry, or combinations thereof, without limitation. In an embodiment, at least a portion of the PDC 10 may have a substantially cylindrical shape. For example, the PDC 10 may include a substantially cylindrical outer surface surrounding a central axis 28 extending through PDC 10, as illustrated in FIGS. 1 and 2. In an embodiment, the side surface 15 and the PCD side surface 22 may have substantially the same outer diameter $OD_1$ relative to the central axis 28, as shown in FIG. 2. In other embodiments, the side surface 15 and the PCD side surface 22 may each have a different outer diameter relative to central axis 28 (not shown).

The substrate 12 may be formed of any suitable material on which the PCD table 14 may be formed and/or bonded. For example, the substrate 12 may include a plurality of tungsten carbide grains cemented together with a cementing constituent that can serve as a metal-solvent catalyst, such as a cobalt-cemented tungsten carbide material and/or any other suitable material. For example, the cementing constituent may comprise, for example, cobalt, nickel, iron, or alloys thereof. The substrate 12 may also include any other suitable material including, without limitation, other carbides such as titanium carbide, niobium carbide, tantalum carbide, vanadium carbide, chromium carbide, or combinations of any of the preceding carbides cemented with iron, nickel, cobalt, or alloys thereof. It should be noted that the PCD table 14 may be replaced by any suitable superabrasive material or combination of materials including, for example, cubic boron nitride, silicon carbide, mixtures thereof, or composites including one or more of the foregoing materials, without limitation.

The PCD table 14 may be formed using any suitable technique. For example, PCD table 14 may be formed by subjecting a plurality of diamond particles (e.g., diamond particles having an average particle size between approximately 0.5 µm and approximately 150 µm) to an HPHT sintering process in the presence of a metal-solvent catalyst, such as cobalt, nickel, iron, combinations thereof, alloys thereof, or any other suitable group VIII element or alloys thereof. During the HPHT sintering process, adjacent diamond crystals in a mass of diamond particles may become bonded together, forming the PCD table 14. Further, during the HPHT sintering process, diamond grains may also become bonded to interface 26 of the substrate 12.

The resulting sintered PCD table 14 may include a matrix of bonded diamond grains exhibiting diamond-to-diamond bonding (e.g., $sp^3$ bonding) therebetween and interstitial regions defined between the bonded diamond grains. Such interstitial regions may be at least partially filled with various materials, including, for example, cobalt and/or other metal-solvent catalyst, tungsten, tungsten carbide, or combinations thereof to facilitate bonding between adjacent diamond particles.

In other embodiments, the PCD table 14 may be removed from the substrate 12 by machining (e.g., grinding or electrical discharge machining), substantially completely leached of the metal-solvent catalyst used in formation thereof, and re-attached to another substrate 12. For example, the leached PCD table may bonded to another substrate 12 in another HPHT process in which a cementing constituent from the substrate infiltrates, for example, substantially fully or at least partially, into the leached PCD table.

Following HPHT processing, various materials, such as a metal-solvent catalyst or a metallic infiltrant, may still remain in interstitial regions within PCD table 14, and may reduce the thermal stability of PCD table 14 at elevated temperatures, such as temperatures developed during drilling and/or cutting operations. Such portions of the PCD table 14 may be excessively worn and/or damaged during the drilling and/or cutting operations.

Removing the metal-solvent catalyst and/or other materials from the PCD table 14 may improve a wear resistance of the PCD table 14, a heat resistance of the PCD table 14, a thermal stability of the PCD table 14, or combinations thereof particularly in situations in which the PCD table 14 may be exposed to elevated temperatures, such as during drilling. A metal-solvent catalyst and/or other materials may be removed from a selected region 17 of the PCD table 14 using any suitable technique, including, for example, an leaching process. For this reason, substantially all of the metal-solvent catalyst and/or metallic infiltrant in the selected region 17 of the PCD table 14 (e.g., adjacent to the working surface 20, the chamfer 24, and the PCD side surface 22) may subsequently be depleted of the metal-solvent catalyst and/or metallic infiltrant via the leaching process by exposure to a suitable acid (e.g., aqua regia, nitric acid, hydrofluoric acid, or other suitable acid). For example, at least a portion of the PCD table 14 may be immersed in the acid for a period of time depending on the process employed. The leaching time and completeness of the metal-solvent catalyst or infiltrant removal depends on the porosity of the PCD table 14, among other factors. For example, decreased porosity may decrease the completeness of depletion of the metal-solvent catalyst/metallic infiltrant and/or may require additional leaching time to reach a desired amount or geometry of removal.

The leaching process may remove at least most of the metal-solvent catalyst and/or infiltrant to a selected depth "d" as measured from any one or more of the superabrasive face 20, the PCD side surface 22, or the chamfer 24. However, a small concentration of the metal-solvent catalyst and/or infiltrant may be present within the leached region (e.g., the selected region 17) after the leaching. For example, it is typical for an average concentration of residual metal-solvent catalyst or infiltrant to be about 0.5% to about 2% by weight, more typically about 0.9% to about 1% by weight, after leaching within the leached region. Generally, the selected depth "d" may be less than about 100 µm, greater than 250 µm, about 200 µm to about 1000 µm, greater than 300 µm to about 425 µm, about 180 µm to about 265 µm, greater than 350 µm to about 400 µm, greater than 350 µm to about 375 µm, about 300 µm to about 900 µm, about 400 µm to about 800 µm, about 500 µm to about 700 µm, about 600 µm to about 800 µm, or about 10 µm to about 800 µm. In an embodiment, the depth d may vary depending on whether the depth d is measured inwardly from any one or more of the superabrasive face 20, the PCD side surface 22, or the chamfer 24.

A protective leaching cup may be used to protect a selected portion of the PCD element from the leaching agent, as disclosed in U.S. patent application Ser. No. 14/084,058, entitled "Protective Leaching Cups, Systems, and Methods of Use." Any of the leaching cups disclosed in U.S. patent application Ser. No. 14/084,058 may be evaluated, analyzed, inspected, or combinations thereof using the X-ray systems and methods disclosed herein. To ensure that the protective leaching cup functions as desired, embodiments disclosed herein may employ an X-ray system and methods for non-destructively inspecting and checking tooling, fixtures, parts loaded in protective leaching cups, protective leaching trays (e.g., prior to or after leaching), or combinations thereof. For example, embodiments disclosed herein may be used to analyze a seal region between the protective leaching cup and the part being leached. X-ray inspection may further help determine where the seal of the protective leaching cup is positioned relative to the PDC being leached, which may affect leach profiles or depths of a PCD table of the PDC being leached. X-ray inspection may also be used to determine a presence of and/or understand gaps between the protective leaching cup and the part being leached, or gaps between the protective leaching cup and the tray holding the protective leaching cup. For example, some gaps may be formed due to trapped gas(es). X-ray inspection may also be used to help analyze different tooling and fixtures formed of various materials to prepare the parts for leaching. X-ray inspection may be used to monitor the leaching process as the leaching process progresses.

Figure 3:
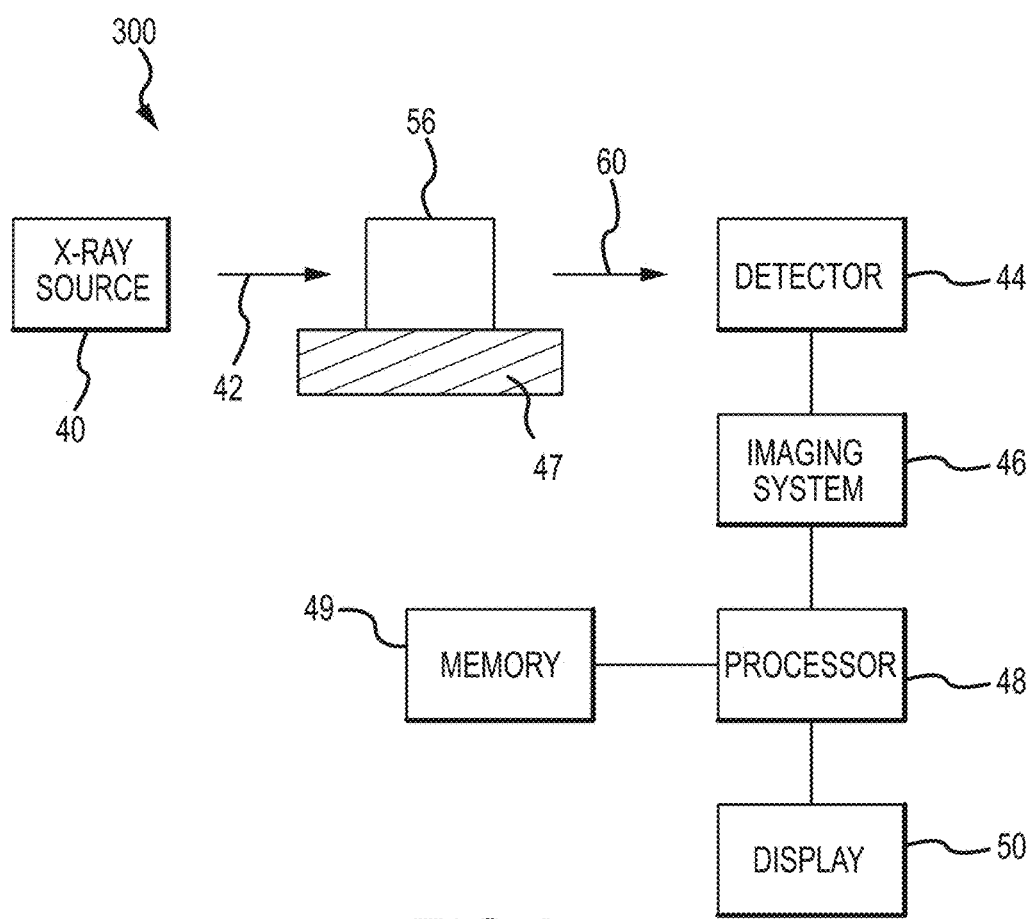
FIG. 3 is a system diagram illustrating X-ray inspection of an assembly such as a PDC according to an embodiment.

FIG. 3 is a system diagram of an X-ray inspection system 300 configured for inspecting an assembly according to an embodiment. The X-ray inspection system 300 may include an X-ray source 40, an X-ray detector 44, and an imaging system 46 coupled to the X-ray detector 44. The X-ray inspection system 300 may also include a processor 48 coupled to the imaging system 46, a memory device 49 coupled to the processor, and a display 50 coupled to the processor 48.

In operation, to create an X-ray image, the X-ray source 40 outputs X-rays 42 toward an assembly 56 that is supported by a supporting member 47. The assembly 56 may be a PDC, a protective leaching cup, or a tray. The assembly 56 may also be a protective leaching cup that includes a PDC therein. The assembly 56 may also be a PDC in the protective leaching cup that sits in a tray. It should be appreciated that the assembly 56 may vary from one embodiment to the next.

Some X-rays are absorbed by the assembly 56. The absorption may vary with the density and the composition of the assembly 56. Some X-rays may be transmitted through the assembly 56. The X-ray source 40 may be placed on one side of the assembly 56, while the detector 44 may be placed on an opposite side of the assembly 56 to receive the transmitted X-rays 60 through the assembly 56. The detector 44 may be a digital detector or a film.

In an embodiment, the X-ray system 300 may be selected from a number of different commercially available X-ray systems. For example, the X-ray system 300 may be the commercially available General Electric Phoenix Nanome|x180, which is an ultra high-resolution nano focus X-ray inspection system designed for inspecting high-quality assemblies. The General Electric Phoenix Nanome|x180 system can be used for 2D X-ray inspection as well as for full 3D computed tomography.

The imaging system 46 is electrically coupled to the detector 44 and may convert the X-rays detected in the detector 44 into a visible image. The processor 48 is electrically coupled to the imaging system 46, and may manipulate the visible image to form a 2D image of the internal structure of the assembly 56. The 2D image may be stored in the memory device 49. The 2D image may be viewed on the display 50 electrically coupled to the processor 48. For example, the imaging system 46, the processor 48, the memory device 49, and the display 50 may form part of a computing system such as a desktop or laptop computer.

In an embodiment, the detector 44 may also detect phase variations of the X-rays transmitted through the assembly 56. The imaging system 46 may convert the phase variations in the X-rays into intensity variations to provide X-ray phase contrast imaging. The phase contrast imaging may be used to achieve a higher contrast than the normal absorption process to enable observing finer details of the assembly 56. The phase contrast imaging is at least partially based upon variations in refractive indexes of the assembly 56.

FIGS. 4A and 4B are side views of an assembly to be X-ray imaged according to an embodiment. FIG. 4A shows an expansion apparatus positioned within a protective leaching cup in a first position. FIG. 4B shows the expansion apparatus of FIG. 4A positioned within the protective leaching cup of FIG. 4A in a second position.

First, as shown in FIG. 4A, a protective leaching cup 54 may include a base portion 59 and a sidewall 58 defining a receiving space for surrounding at least a portion of the PDC 10. The protective leaching cup 54 may be formed of any suitable size, shape and/or geometry, without limitation. In an embodiment, portions of protective leaching cup 54 may have a substantially cylindrical outer periphery extending about a central axis 63. The base portion 59 and the sidewall 58 may define the receiving space within protective leaching cup 54. An opening may be defined in a portion of the protective leaching cup 54 opposite the base portion 59. A seal region 55 of the protective leaching cup 54 may be configured to contact a selected portion of the PDC 10 (e.g., at the PCD table 14 and/or substrate 12), thereby forming a seal between the protective leaching cup 54 and the PDC 10. For example, the seal region 55 may seal against the PDC 10 at or near a bottom of the chamfer 24 of the PCD table 14, below the chamfer 24 against the side surface 22 of the PCD table 14, or at or near the interface 26 between the PCD table 14 and the substrate 12.

The protective leaching cup 54 may be sized and configured such that an interference fit is created between the protective leaching cup 54 and the PDC 10. In an embodiment, the seal region 55 of the protective leaching cup 54 may exert a contact pressure on a side surface (e.g., the PCD side surface 22 and/or the side surface 15 of the substrate 12) of the PDC 10 such that PDC 10 creates an interference fit with the seal region 55. In an embodiment, the interference fit may cause the seal region to exceed a yield stress of the material comprising the seal region 55. Thus, the seal region 55 may help restrict movement of the PDC 10 within the protective leaching cup 54 due to physical interference between the PDC 10 and the seal region 55.

In some embodiments, the seal region 55 may be formed as part of the leaching cup 54 and may extend inwardly from the sidewall 58. For example, the seal region 55 may protrude inwardly from the sidewall 58. In some embodiments, the seal region 55 may be a separate component, such as a seal ring (e.g., an O-ring), which may be formed of a different material from the sidewall 58 and may be placed at a desired position to seal a portion of the PCD element from a leaching agent.

With the assistance of X-ray imaging, the seal region 55 may be inspected non-destructively to help understand, analyze, evaluate, or combinations thereof the seal region 55 between the PDC 10 and the protective leaching cup 54. For example, the seal region 55 may be analyzed to determine whether it is properly positioned or configured relative to the PDC 10. This may help achieve a specified leaching profile or depth in the PCD table 14 of the PDC 10.

As shown in FIG. 4A, trapped gas(es) may cause a base portion gap 53 to be formed between the rear face 18 of the PDC 10 and an inner rear surface 51 of the base portion 59 of the protective leaching cup 54, preventing or limiting proper positioning of the PDC 10 in the protective leaching cup 54. The gap 53 may be viewed by X-ray imaging prior to leaching, followed by using an expansion apparatus to help evacuate the trapped gas(es), such that trapped gas(es) do not substantially affect the position of the PDC 10 in the protective leaching cup 54 during leaching.

Now, turning to an expansion apparatus that may be viewed by X-ray imaging, as shown in FIGS. 4A and 4B, an expansion apparatus 52 is used for positioning the PDC 10 within the protective leaching cup 54 and/or for expanding a portion of the protective leaching cup 54 to at least partially evacuate gas(es) trapped between the PDC 10 and the protective leaching cup 54. The expansion apparatus 52 may include a main body 64, an expansion feature 65, and a contact member 66. In an embodiment, the expansion apparatus 52 may be generally centered about a central axis 67. According to some embodiments, a user or a machine may grasp the main body 64 of the expansion apparatus 52 during operation. The expansion feature 65 of the expansion apparatus 52 may be shaped and configured to temporarily expand and/or otherwise temporarily deform at least a portion of the protective leaching cup 54 outwardly. The expansion feature 65 may include at least one sloped portion 68. In an embodiment, the contact member 66 may extend from the expansion feature 65 of the expansion apparatus 52 in a direction substantially parallel to the central axis 67. The contact member 66 may have a contact face 71 configured to contact a portion of the working surface 20 of the PDC 10 positioned within the protective leaching cup 54.

With the X-ray imaging technique, the gap 53, the rear face 18 of the PDC 10, and the inner rear surface 51 of the base portion 59 of the protective leaching cup 54 may be viewed non-destructively to help determine if there are gas(es) trapped between the protective leaching cup 54 and the PDC 10 or if the PDC 10 is otherwise positioned incorrectly. If there are trapped gas(es), the expansion apparatus 52 may be used to help evacuate the trapped gas(es). The central axis 67 of the expansion apparatus 52 may be aligned with the central axis 63 of the protective leaching cup 54, such that the protective leaching cup 54 may be deflected generally uniformly circumferentially during an expansion of the protective leaching cup 54 to help evacuate trapped gas(es) during leaching.

As shown in FIG. 4B, the expansion apparatus 52 may be aligned with the protective leaching cup 54 such that a substantially uniform gap 57 may be formed between the seal region 55 of the PDC 10 and the sidewall 58 when the expansion apparatus 52 is forced down to bend the protective leaching cup 54. Once properly aligned with the protective leaching cup 54, the expansion apparatus 52 may force the protective leaching cup 54 to deform such that one or more expansion gaps 57 may be formed between the protective leaching cup 54 and the PDC 10. Specifically, as shown in FIG. 4B, the expansion gaps 57 may be formed between an inner side surface 61 of the protective leaching cup 54 and a side surface of the PDC 10. The expansion gaps 57 may provide a passage for evacuating gas(es) trapped between the protective leaching cup 54 and the PDC 10. The sidewall gap 62 may also facilitate migration of trapped gas(es) to expansion gaps 57 from various regions of protective leaching cup 54 including, for example, gas(es) trapped in base portion gap 53 shown in FIG. 4A. After positioning the PDC 10 in the protective leaching cup 54, X-ray imaging may be used to verify that the gap 53 is reduced to zero, and/or that the PDC 10 is positioned correctly. Further, X-ray imaging may be used to evaluate the geometry of the leaching cup. Specifically, in an embodiment, the seal region 55 may be inspected for damage, deformation, size, position, configuration, or combinations thereof.

Prior to loading the PDC 10 into the protective leaching cup 54, the protective leaching cup 54 may be preheated to an elevated temperature to facilitate positioning of the PDC 10 within protective leaching cup 54. The preheating may help evacuate the trapped gas(es).

Figure 5:
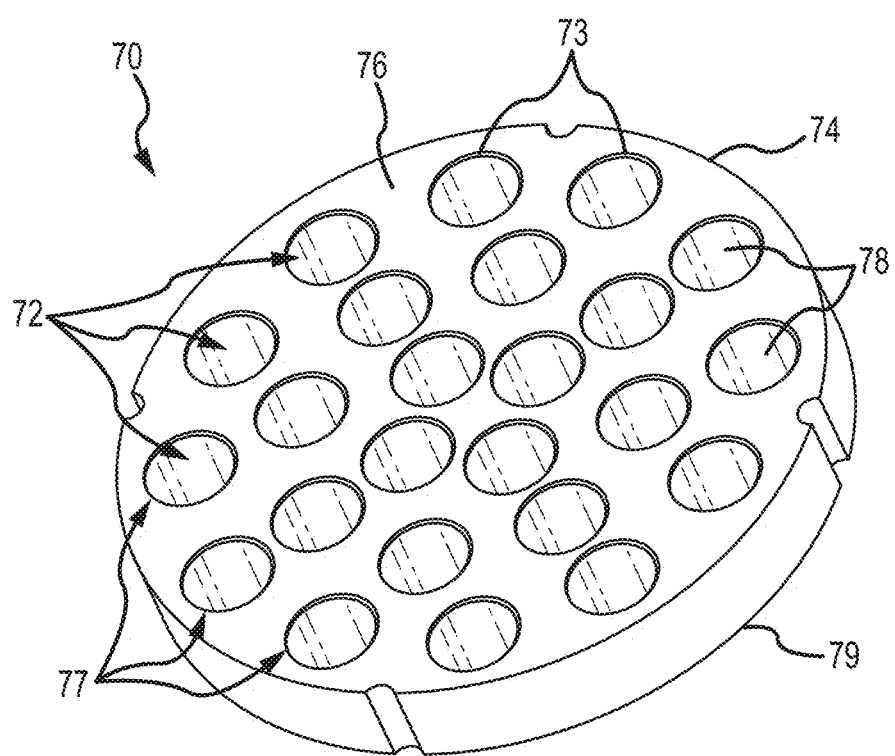
FIG. 5 is an isometric view of a leaching tray for X-ray inspection according to an embodiment.

The assembly 56 shown in FIG. 3 may also be a tray that may be viewed by X-ray imaging. FIG. 5 is an isometric view of a leaching tray according to an embodiment. The leaching tray 70 may be used for holding multiple PDCs 10 each of which is positioned within a leaching cup during leaching. The leaching tray 70 includes a number of tray receptacles 72, each of which is configured to hold one of the protective leaching cups 54 that seals a respective one of PDCs 10 during leaching. The tray receptacles 72 may extend through an entire thickness of a tray body 74, from front openings 77 defined in front surface 76 to back openings (not shown) defined in a back surface 79. In some embodiments, the tray receptacles 72 may extend only partially through tray body 74 so that tray receptacles 72 are open to either the front surface 76 or the back surface 79.

Each of the tray receptacles 72 may be defined by a receptacle surface 78 and a receptacle chamfer 73 extending between front surface 76 and receptacle surface 78. In some embodiments, the tray receptacle 72 may also be defined by another receptacle chamfer extending between the back surface 79 and the receptacle surface 78. The receptacle surface 78 may exhibit any suitable shape, such as a substantially cylindrical shape or any other shape suitable to receive a protective leaching cup. The leaching tray 70 may be formed of any suitable material. For example, in an embodiment, the leaching tray 70 may include one or more polymeric materials.

The receptacle surface 78 may closely surround and/or abut the protective leaching cup 54 such that the protective leaching cup 54 and the PDC 10 disposed therein, may be secured within the leaching tray 70 during leaching. The receptacle surface 78 may have an inner diameter that is approximately the same as or smaller than an outer diameter of the protective leaching cup 54, such that an interference fit may be created between the protective leaching cup 54 and the receptacle surface 78 to secure the protective leaching cup 54 within the tray receptacle 72 during leaching. In some embodiments, prior to loading the protective leaching cup 54 into the leaching tray 70, the leaching tray 70 may be preheated to an elevated temperature to facilitate positioning of the protective leaching cup 54 within the tray receptacle 72.

Figure 6:
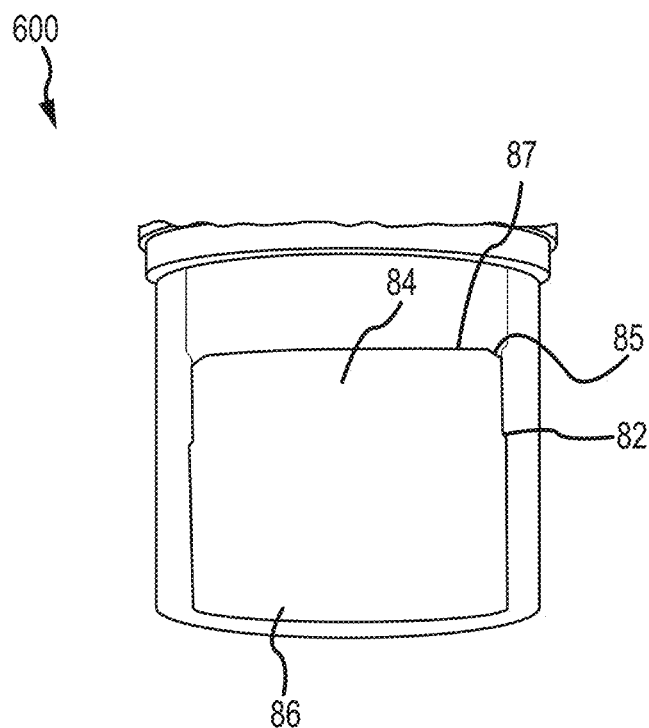
FIG. 6 is a representation of an X-ray image of a PCD element.
Figure 7A:
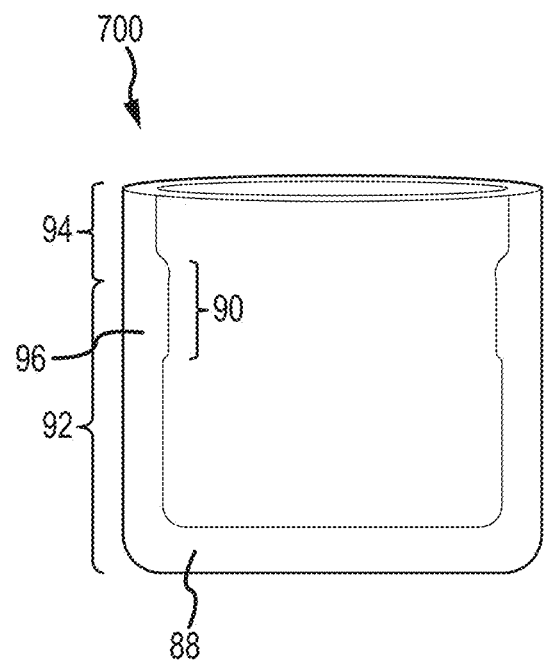
FIG. 7A is a representation of an X-ray image of a protective leaching cup.
Figure 7B:
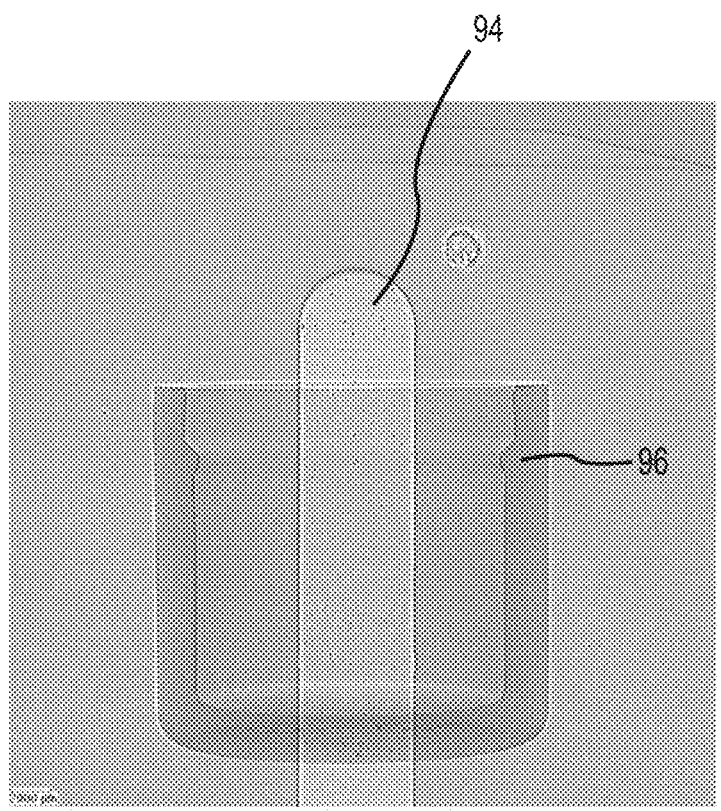
FIG. 7B illustrates an actual X-ray image of a protective leaching cup according to an embodiment.

FIGS. 6-9 illustrate various representations of X-ray images of a protective leaching cup, a PDC, and the PDC in the protective leaching cup that may sit in a tray. FIG. 6 shows a schematic representation of an X-ray image 600 that shows a PDC including a PCD table 84 and a substrate 86 attached to the PCD table 84 at an interface 82. The representation of X-ray image 600 also shows that the PCD table 84 includes a chamfer 85 near a top surface 87 of the PCD table 84. The chamfer 85 may be used to help control the leaching depth of the PCD table 84. FIG. 7A shows a schematic representation of an X-ray image 700 that shows a protective leaching cup including a base portion 88, and a sidewall 96 that includes an upper portion 94 and a lower portion 92 joined to the upper portion 94 at a seal region 90. The representation of X-ray image 700 also reveals that the seal region 90 extends inwardly from the sidewall 96. FIG. 7B illustrates an actual X-ray image of a protective leaching cup according to an embodiment. A cross-section of the sidewall 96 of the leaching cup is visible in the X-ray image. Structure 94 is part of fixturing used to hold the protective leaching cup during X-ray inspection, which is behind the protective leaching cup.

Figure 8A:
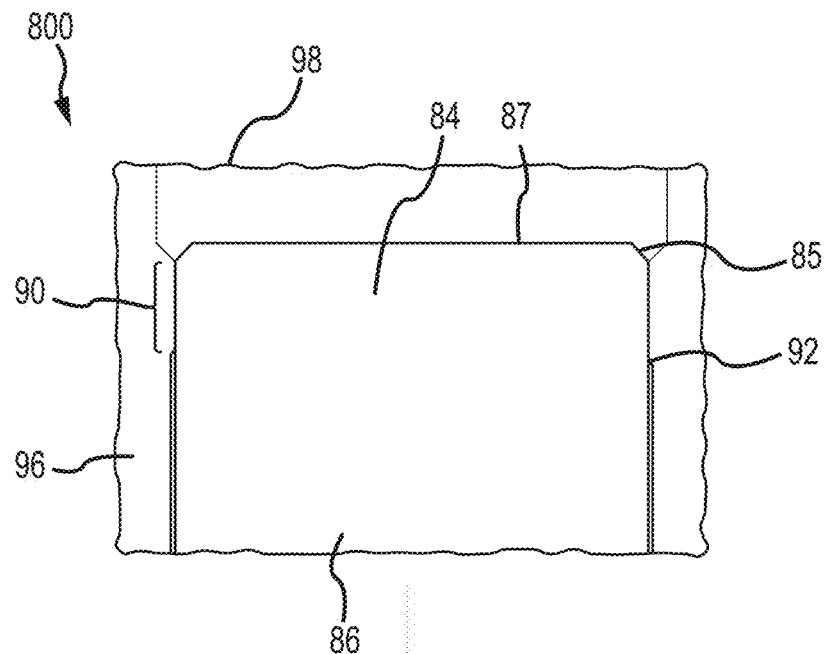
FIG. 8A is a representation of an X-ray image of the PCD element of FIG. 6 in the protective leaching cup of FIG. 7A according to an embodiment.

FIG. 8A illustrates a schematic representation of an X-ray image of an embodiment of a PDC in a protective leaching cup. The representation 800 shows that the PDC abuts against the lower portion 92 of the sidewall 96 of the protective leaching cup and the chamfer 85 of the PCD table 84 is positioned at or above the seal region 90 of the protective leaching cup, such that the chamfer 85 of the PCD table 84 is exposed to a leaching agent while the region of the PCD element at or below the seal region 90 is protected from being exposed to the leaching agent. The representation 800 also shows that the top surface 98 of the protective leaching cup extends above the top surface 87 of the PCD element.

Figure 8B:
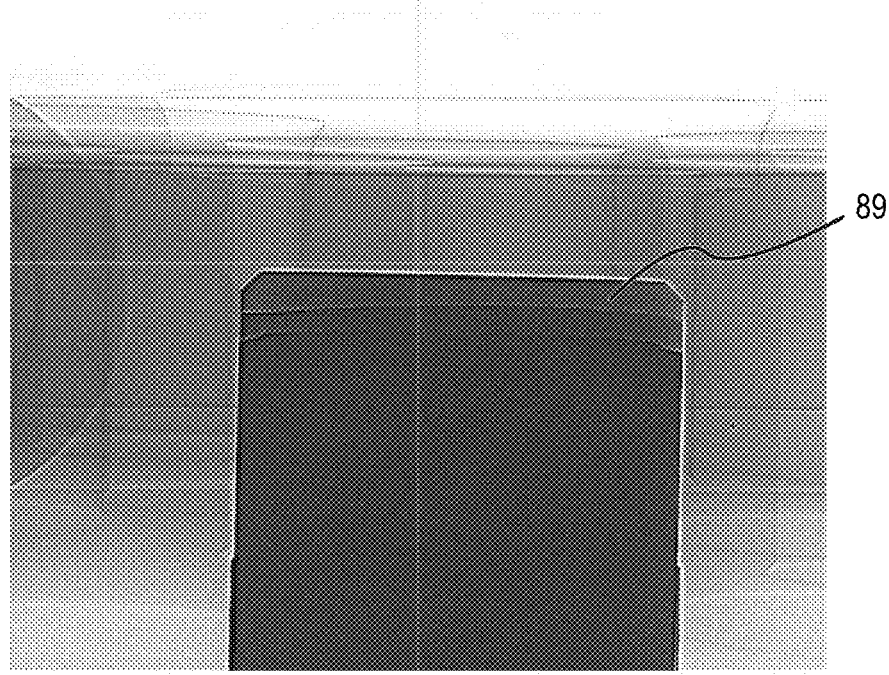
FIG. 8B illustrates an actual X-ray image of a PCD element in a protective leaching cup prior to leaching according to an embodiment.
Figure 8C:
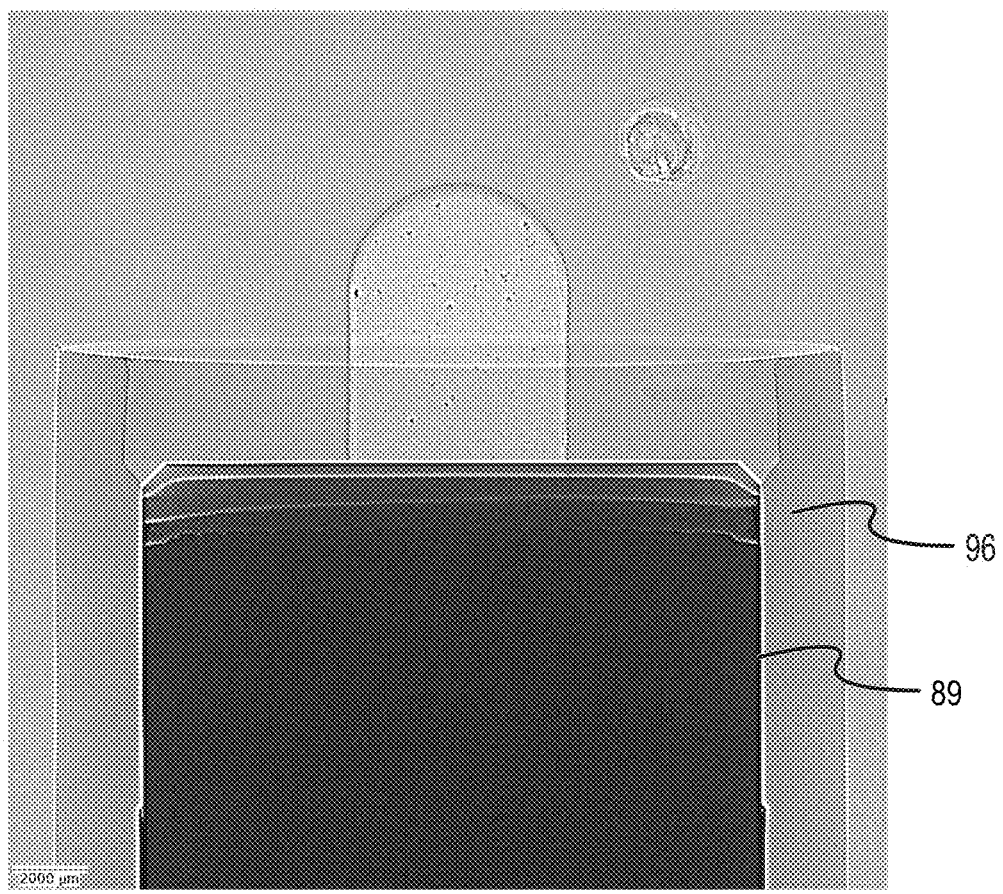
FIG. 8C illustrates an actual X-ray image of a PCD element in a protective leaching cup after leaching the PCD element according to an embodiment.

FIG. 8B illustrates an actual X-ray image of a PCD element 89 in a protective leaching cup prior to leaching according to an embodiment. FIG. 8C illustrates an actual X-ray image of a PCD element 89 in a protective leaching cup after leaching according to an embodiment. The PCD element 89 exhibits a relatively dark X-ray image, while the protective leaching cup 96 formed of a polymer reveals a relatively light X-ray image. The darkness of the tray is similar to the leaching cup in the X-ray image (FIG. 8B). The different intensities of the X-ray images are due to the PDC absorbing relatively more X-rays than the plastic protective leaching cup or the plastic tray, which results in the light X-ray image for the PDC than the protective leaching cup or tray.

Figure 9:
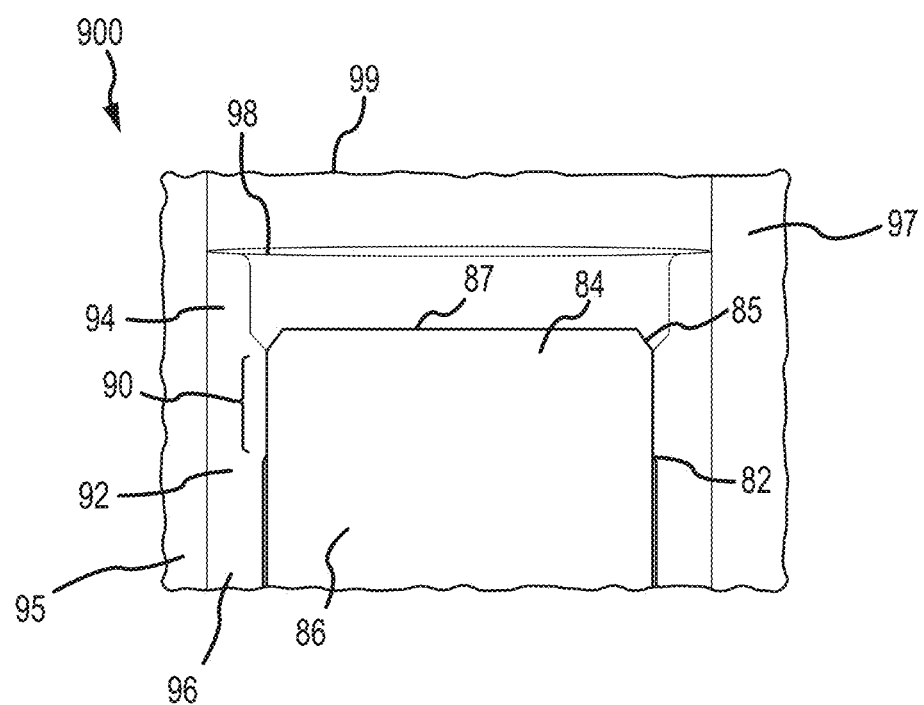
FIG. 9 is a representation of an X-ray image of the PCD element of FIG. 6 in the protective leaching cup of FIG. 7 that sits in a tray according to an embodiment.

FIG. 9 illustrates a schematic representation of an X-ray image of an embodiment of the PDC in the protective leaching cup that sits in a tray. The tray also has a lighter image than the PCD element because the tray may be formed of a polymer. The representation 900 shows that the PDC including the PCD table 84 attached to the substrate 86 sits inside the sidewall 96 of the protective leaching cup. The seal region 90 of the sidewall 96 of the protective leaching cup is positioned against the sidewall 95 of the tray 97. The representation 900 also reveals that the top surface 98 of the protective leaching cup is below the top surface 99 of the tray.

The X-ray technique may also be used to non-destructively inspect defects of a PDC or PCD element during processing or even a used cutter. For example, X-ray images may be acquired of a surface of the PDC to see if there are any defects in the PCD element, such as plumes, cracks, pits or agglomerations.

Referring back to FIGS. 1 and 2, the leached PDC 10 may include some defects (e.g., pits, cracks, metal clusters, or combinations thereof). In some embodiments, the X-ray imaging may be used for inspection of such defects. For example, X-ray imaging may be used to locate clusters in the leached PCD table 14. The metal clusters may be formed as a result of incomplete leaching. The distribution of residual metal-solvent catalyst and/or metallic infiltrant within the leached portion may not be substantially uniform. In other words, the residual metal-solvent catalyst and/or infiltrant may be present as metal clusters including a plurality of portions in which the metal clusters of metal-solvent catalyst or infiltrant may be surrounded by diamond grains and interstitial regions containing little or no metal-solvent catalyst or infiltrant. The presence of such metal clusters may result in decreased wear resistance and/or thermal stability within the subregion in which the metal cluster is located The substrate 12 may also have undesirable defects, such as abnormal grain growth ("AGG") or plumes. The AGG of the substrate 12 or plumes may also be inspected by X-ray imaging. During the HPHT process, tungsten carbide grains in a region of the cemented tungsten carbide substrate 12 located adjacent to the PCD table 14 may experience significant AGG, which may project from the cemented tungsten carbide substrate 12 into the PCD table 14 to thereby introduce stress concentrations and/or defects that may cause damage when loaded during subterranean drilling operations.

Furthermore, the presence of other interstitial constituents such as by-products of the leaching process (e.g., light chemical elements and/or light molecules, salts, oxides, or combinations thereof) may become trapped within the leached region (e.g., the selected region 17) of PCD table 14. For example, the light chemical elements and/or light molecules may include hydrogen, oxygen, nitrogen, water, other contaminants (e.g., salts and/or oxides), or combinations of the foregoing. The presence of such contaminants may also be detrimental to the performance characteristics of the PCD table 14. The contaminants may be detected by using neutron radiation imaging technique as disclosed in related U.S. patent application Ser. No. 13/267,026 entitled "Detection of One or More Interstitial Constituents in a Polycrystalline Diamond Element by Neutron Radiographic Imaging," which is incorporated by reference in its entirety.

Additionally, X-ray imaging may be used to distinguish certain intermediate compounds (e.g., intermetallic compounds) present in the interstitial regions between bonded diamond grains of the PCD element 14 from a metal-solvent catalyst. For example, the X-ray imaging may be used to distinguish one or more phosphorous and/or boron-containing intermediate compounds and/or an infiltrant (e.g., silicon) from cobalt present in the interstitial regions between bonded diamond grains of the PCD table 14 as disclosed in U.S. patent application Ser. Nos. 14/086,283 and 14/304,631, the disclosures of which are incorporated herein, in their entirety, by this reference.

Figure 10:
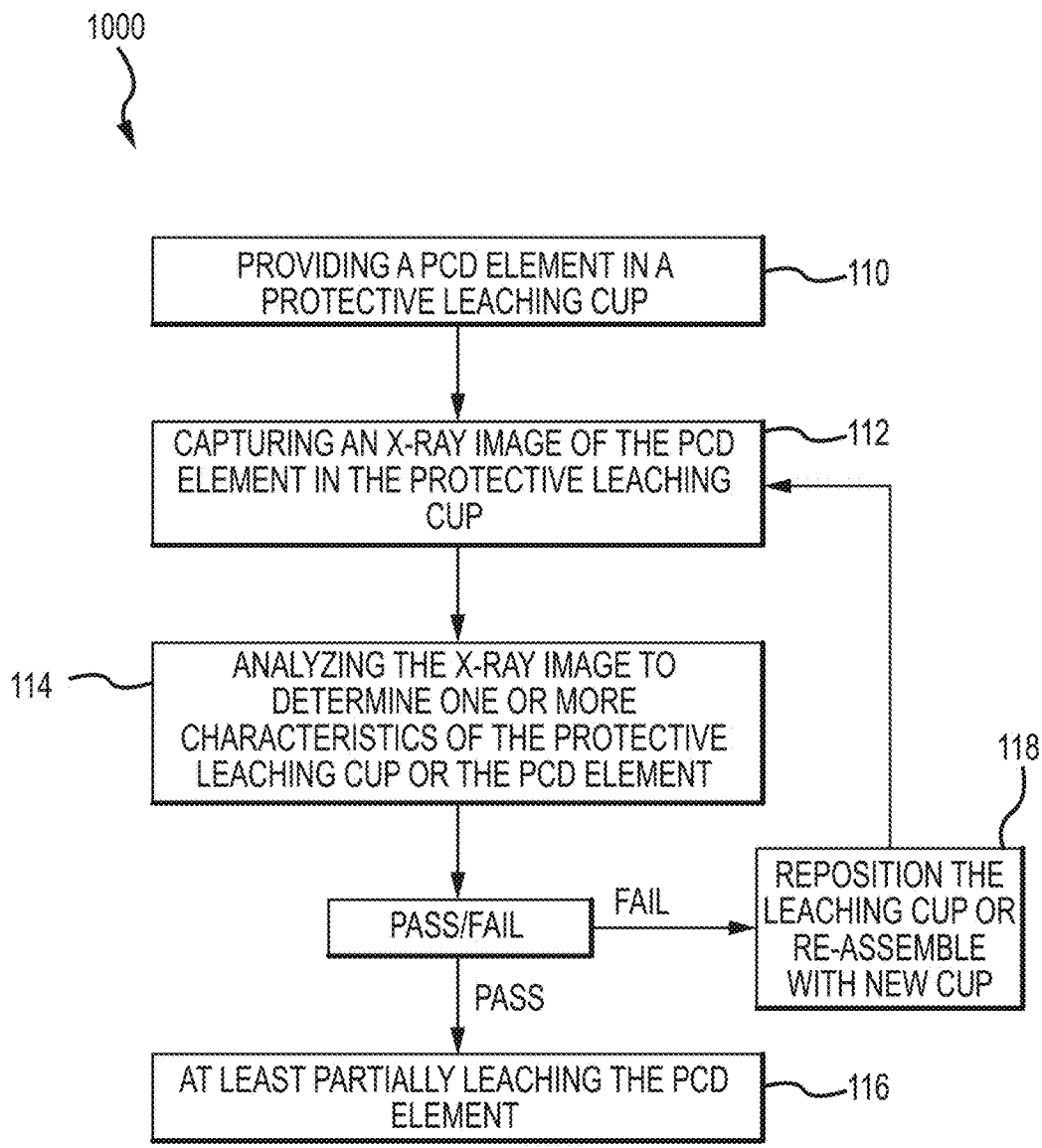
FIG. 10 is a flow chart of a method of inspecting a PCD element in a protective leaching cup by X-ray imaging prior to leaching the PCD element according to an embodiment.
Figure 11:
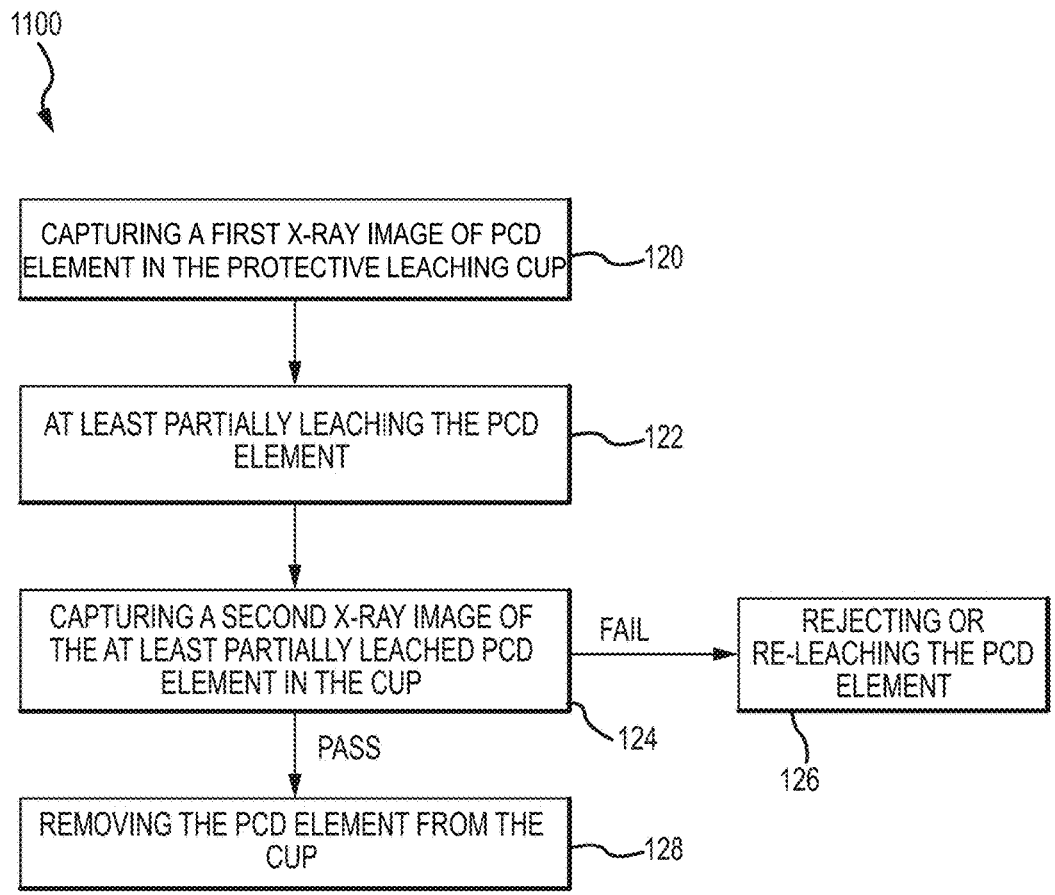
FIG. 11 is a flow chart of a method of leaching a PCD element in a protective leaching cup and inspecting a leached PCD element in the protective leaching cup according to an embodiment.
Figure 12:
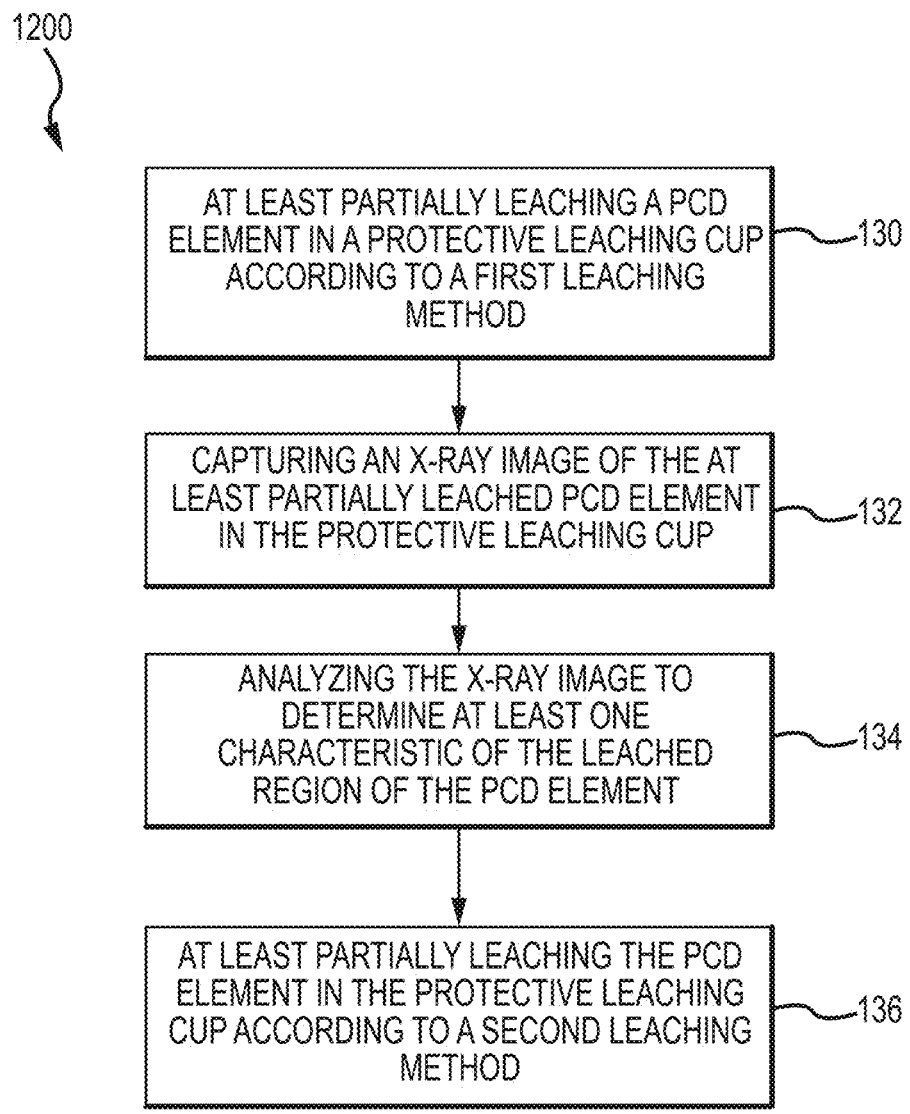
FIG. 12 is a flow chart of a method of selectively leaching a PCD element to obtain different leached regions and inspecting by X-ray according to an embodiment.

FIGS. 10-12 are flow charts illustrating different methods according to various embodiments for inspecting and/or analyzing a PCD element and a protective leaching cup holding in the PCD element. In the methods shown in FIGS. 10-12, the PCD element is described as the PDC 10 shown in FIGS. 1 and 2 and the protective leaching cup is described as the protective leaching cup 54 shown in FIGS. 4A and 4B. However, it should be understand that other types of superabrasive elements and protective leaching cup configurations may be used in the disclosed methods and with the disclosed X-ray systems, without limitation.

FIG. 10 is a flowchart illustrating a method 1000 of leaching a PCD element in a protective leaching cup using X-ray imaging for inspection prior to leaching according to an embodiment. The method 1000 may start with providing the PCD element in the protective leaching cup 54 in act 110. The protective leaching cup 54 is configured to expose a selected portion of the PDC 10 to a leaching agent. The protective leaching cup 54 may be formed of plastic or other suitable material.

The method 1000 may also include capturing an X-ray image of the PCD element in the protective leaching cup in act 112. The method 1000 may also include analyzing the X-ray image to determine one or more characteristics of the protective leaching cup or the PCD element at act 114. In some embodiments, the one or more characteristics may be a position of the seal region 55 of the protective leaching cup 54 relative to the PDC 10. In some embodiments, the one or more characteristics may be a gap between a bottom of the PDC 10 and the base portion 59 of the protective leaching cup 54.

In a particular embodiment, the act of capturing an X-ray image may include placing the PDC 10 in the protective leaching cup 54, exposing the PDC 10 in the protective leaching cup 54 to X-rays emitted from the X-ray source 40, positioning the detector 44 to detect the X-rays that passes through the PDC 10 and the protective leaching cup 54, and generating a 2D X-ray image that illustrates the one or more sealing characteristics.

In act 116, the method 1000 may further include at least partially leaching the PCD element if the characteristics of the protective leaching cup 54 or the PCD element satisfies a selected criteria, such as the gap between a bottom of the PDC 10 and the base portion 59 of the protective leaching cup 54 is nearly zero or the position of the PCD element is as desired.

If the X-ray shows that the PCD element is not properly positioned in the leaching cup 54, the PCD element may be re-positioned in the protective leaching cup 54, such as through removing gas(es), or the PCD element may be re-assembled with a new protective leaching cup in act 118. For example, positioning the PDC 10 in the protective leaching cup 54 by using the expansion apparatus 52 to position the seal region 55 adjacent to a selected portion of the PCD table 14 and/or substrate 12 to control a leaching depth of the PCD table 14, a leaching profile of the PCD table 14, to evacuate trapped gas(es), or combinations thereof. After re-positioning the PCD element in the protective leaching cup or re-assembling the PCD element in a new leaching cup, acts 114, 116, 118 may be repeated as needed or desired.

The method 1000 may also include placing the protective leaching cup 54 in the tray 70 (FIG. 5) that is configured to hold a plurality of protective leaching cups; and capturing an X-ray image of the protective leaching cup 54 in the tray.

FIG. 11 is a flow chart illustrating a method 1100 of leaching a PCD element in a protective leaching cup 54 and inspecting a leached PCD element in the protective leaching cup 54 according to an embodiment. The method 1100 may include capturing a first X-ray image of the PCD element in the protective leaching cup 54 in act 120. For example, the first X-ray image may show a gap 53 between the bottom of the PDC 10 and the base portion 59 of the protective leaching cup 54. In an embodiment, the method 1100 may include preheating the protective leaching cup 54 prior to capturing the first X-ray image.

If the first X-ray image demonstrated that the PDC 10 is properly positioned in the protective leaching cup 54 and/or the protective leaching cup 54 seals adequately against the PDC 10, the method 1100 may also include at least partially leaching the PCD element at act 122. For example, if the X-ray image shows the gap 53, gas(es) may be trapped between the PDC 10 and the protective leaching cup 54, which may cause the PDC 10 to be displaced during leaching and thereby reduce the accuracy of the resultant leach depth profile of the PCD table 14. Thus, the method 1100 may further include expanding the protective leaching cup 54 to evacuate the trapped gas(es) between the PDC 10 and the protective leaching cup 54, for example, the protective leaching cup 54 may be expanded by using the expansion apparatus 52 as discussed with respect to FIG. 4B. Following the act of expanding the protective leaching cup, the method 1100 may include forcing the PDC 10 down toward the base portion 59 of the protective leaching cup 54 prior to capturing a second X-ray image.

Then, in act 124, the method 1100 may also include capturing a second X-ray image of the PDC 10 in the at least partially leached protective leaching cup. For example, the leached region may be inspected by the second X-ray image to inspect a leach profile or leach depth thereof. If the leach profile of the PCD element is satisfactory, the PCD element may be removed from the protective leaching cup 54 in act 128. If the leach profile is not satisfactory, the PCD element may be re-leached or the protective leaching cup 54 may be rejected in act 126. For example, if the PDC element is re-leached, the PCD element may be re-positioned in the protective leaching cup 54 so that the leach profile generated after re-leaching is more accurate and acceptable.

FIG. 12 is a flow chart illustrating a method 1200 of leaching a PCD element to obtain different leached regions and inspecting the leached regions by X-ray according to an embodiment. The method 1200 may include at least partially leaching a PCD element, such as a PDC 10, in a first protective leaching cup 54 according to a first leaching method in act 130. The method 1200 may also include capturing an X-ray image of the at least partially leached PDC 10 in the protective leaching cup 54 in act 132.

The method 1200 may further include analyzing the X-ray image to determine at least one characteristic of a first leached region of the PCD element in act 134, and at least partially leaching the PCD element in the protective leaching cup 54 according to a second leaching method in act 136. In an embodiment, the method 1200 may include removing the leached PCD element from the protective leaching cup 54 after the act 134 of analyzing the X-ray image and the leached PCD element does not need to be subjected to the act 136 of at least partially leaching the PCD element in the protective leaching cup 54 according to the second leaching method.

In an embodiment, the method 1200 may further include analyzing the X-ray image to determine at least one characteristic of a second leached region of the PCD element leached according to the second leaching method. As a result, the PCD element may have different leached regions. For example, the at least characteristic of the first and/or second leached regions include leach depth and leach profile.

Different leaching methods are disclosed in U.S. Provisional Patent Application No. 62/096,315, which is incorporated herein, in its entirety, by this reference. The PCD element may be leached by exposing the PCD table 14 to a suitable processing solution in the presence of an electrode and applying a charge (e.g., a positive charge) to the PCD table 14 and an opposite charge (e.g., a negative charge) to the electrode. The processing solution may be mixtures of one or more acids. At least a portion of the PCD element may be exposed to the processing solution in each of the first and second leaching methods in act 130 and act 136. The type of acid, the concentration of the acid, the leaching technique, or combinations thereof may vary for leaching different regions of the PCD element in the acts 130 and 136. For example, in the first leaching method of act 130, the PCD table 14 may be electrochemically leached and, in the second leaching method of act 136, the PCD table 14 may be non-electrochemically leached. As another example, in the first leaching method of act 130, the PCD table 14 may be non-electrochemically leached and, in the second leaching method of act 136, the PCD table 14 may be electrochemically leached. As another example, in the first leaching method of act 130, the PCD table 14 may be electrochemically leached using a first leaching process and, in the second leaching method of act 136, the PCD table 14 may also be electrochemically leached in a second leaching process different from the first leaching process.

In some embodiments, the processing solution may include one of a metal salt or an ion. In some embodiments, the processing solution may also include an acid, such as acetic acid, ammonium chloride, arsenic acid, ascorbic acid, carboxylic acid, citric acid, formic acid, hydrobromic acid, hydrofluoric acid, hydroiodic acid, lactic acid, malic acid, nitric acid, oxalic acid, phosphoric acid, propionic acid, pyruvic acid, succinic acid, tartaric acid, or combinations thereof.

In some embodiments, the processing solution may include at least one of an ion or a salt, and an ester of at least one of acetic acid, ammonium chloride, arsenic acid, ascorbic acid, carboxylic acid, citric acid, formic acid, hydrobromic acid, hydrofluoric acid, hydroiodic acid, lactic acid, malic acid, nitric acid, oxalic acid, phosphoric acid, propionic acid, pyruvic acid, succinic acid, or tartaric acid.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall have the same meaning as the word "comprising" and variants thereof (e.g., "comprise" and "comprises").

What is claimed:

1. A method of inspecting a polycrystalline diamond ("PCD") element prior to leaching, the method comprising:
   providing the PCD element in a protective leaching cup, the protective leaching cup configured to expose a selected portion of the PCD element to a leaching agent;
   exposing the PCD element in the protective leaching cup to X-rays emitted from an X-ray source;
   detecting, with a detector, the X-rays that pass through the PCD element and the protective leaching cup; and
   generating an X-ray image of the PCD element in the protective cup that illustrates one or more characteristics from the X-rays received by the detector; and
   analyzing the X-ray image to determine the one or more characteristics of the protective leaching cup or the PCD element.

2. The method of claim 1, wherein the one or more characteristics include a position of a seal region of the protective leaching cup against the PCD element.

3. The method of claim 1, wherein the one or more characteristics include a gap between a bottom of the PCD element and a base portion of the protective leaching cup.

4. The method of claim 1, further comprising:
   placing the protective leaching cup in a tray that is configured to hold a plurality of protective leaching cups; and
   capturing an X-ray image of the protective leaching cup in the tray.

5. The method of claim 1, wherein the PCD element includes a PCD table attached to a substrate.

6. The method of claim 5, wherein the substrate includes a plurality of carbide grains cemented and a cementing constituent.

7. The method of claim 6, wherein the plurality of carbide grains include at least one carbide material selected from a group consisting of tungsten carbide, titanium carbide, niobium carbide, tantalum carbide, vanadium carbide, and chromium carbide, and wherein the cementing constituent includes at least one material selected from a group consisting of cobalt, nickel, iron, cobalt alloys, nickel alloys, and iron alloys.

8. The method of claim 1, wherein the protective leaching cup protects at least one sidewall and a bottom portion of the PCD element.

9. The method of claim 1, wherein the protective leaching cup includes a polymer.

10. A method of leaching a polycrystalline diamond ("PCD") element and inspecting the leached PCD element, the method comprising:
    at least partially leaching the PCD element in a protective leaching cup according to a first leaching method;
    capturing an X-ray image of the leached PCD element in the protective leaching cup;
    analyzing the X-ray image to determine at least one characteristic of a first leached region of the PCD element; and
    at least partially leaching the leached PCD element in the protective leaching cup according to a second leaching method; or removing the leached PCD element from the protective leaching cup after the act of analyzing the X-ray image,
    wherein at least one of the first leaching method or the second leaching method includes exposing at least a portion of the PCD element to a processing solution;
    wherein the processing solution includes at least one member selected from a group consisting of acetic acid, ammonium chloride, arsenic acid, ascorbic acid, carboxylic acid, citric acid, formic acid, hydrobromic acid, hydrofluoric acid, hydroiodic acid, lactic acid, malic acid, nitric acid, oxalic acid, phosphoric acid, propionic acid, pyruvic acid, succinic acid, and tartaric acid.

11. The method of claim 10, further comprising analyzing the X-ray image to determine at least one characteristic of a second leached region of the PCD element.

12. The method of claim 10, wherein the first leaching method is different from the second method.

13. The method of claim 10, wherein the first leaching method is an electrochemical leaching method and the second method is a non-electrochemical leaching method.

14. The method of claim 10, wherein the first leaching method is a non-electrochemical leaching method and the second method is an electrochemical leaching method.

15. A method of leaching a PCD element and inspecting a leached PCD element, the method comprising:
    capturing a first X-ray image of a PCD element in a protective leaching cup, wherein the PCD element includes a PCD table attached to a substrate, the substrate including:

a cementing constituent including at least one material selected from a group consisting of cobalt, nickel, iron, cobalt alloys, nickel alloys, and iron alloys; and a plurality of carbide grains cemented with the cementing constituent, the plurality of carbide grains including at least one carbide material selected from a group consisting of tungsten carbide, titanium carbide, niobium carbide, tantalum carbide, vanadium carbide, and chromium carbide; and at least partially leaching the PCD element to form a leach profile therein;

capturing a second X-ray image of the PCD element in the leaching cup; and if the leach profile of the PCD is satisfactory at least partially based on the second X-ray image, removing the PCD element from the protective leaching cup; or if the leach profile of the PCD element is not satisfactory at least partially based on the second X-ray image, re-leaching the PCD element or rejecting the protective leaching cup.

16. The method of claim 15, further comprising rejecting the protective leaching cup or re-leaching the PCD element if the first X-ray image demonstrates that the leach profile is not satisfactory.

17. The method of claim 16, wherein re-leaching the PCD element includes re-positioning the PCD element in the protective leaching cup.

* * * * *